United States Patent
Sato et al.

(10) Patent No.: US 7,763,652 B2
(45) Date of Patent: Jul. 27, 2010

(54) PROSTAGLANDIN DERIVATIVES

(75) Inventors: Fumie Sato, 2-1-901, Kugenumahigasi, Fujisawa-shi, Kanagawa 251-0026 (JP); Tohru Tanami, Tokyo (JP); Makoto Yagi, Tokyo (JP); Naoya Ono, Tokyo (JP)

(73) Assignees: Taisho Pharmaceutical Co., Ltd., Tokyo (JP); Fumie Sato, Kanagawa (JP)

( * ) Notice: Subject to any disclaimer, the term of this patent is extended or adjusted under 35 U.S.C. 154(b) by 416 days.

(21) Appl. No.: 10/521,115

(22) PCT Filed: Jul. 11, 2003

(86) PCT No.: PCT/JP03/08864

§ 371 (c)(1),
(2), (4) Date: Jan. 12, 2005

(87) PCT Pub. No.: WO2004/007442

PCT Pub. Date: Jan. 22, 2004

(65) Prior Publication Data

US 2006/0094788 A1    May 4, 2006

(30) Foreign Application Priority Data

Jul. 12, 2002 (JP) ............................ 2002-204908

(51) Int. Cl.
*A61K 31/215* (2006.01)
*A61K 31/557* (2006.01)

(52) U.S. Cl. .................. 514/530; 514/573; 560/121; 562/503

(58) Field of Classification Search ............... 562/503; 560/121; 514/530, 573
See application file for complete search history.

(56) References Cited

U.S. PATENT DOCUMENTS 6,329,539 B1    12/2001    Sato et al.

FOREIGN PATENT DOCUMENTS

| EP | 1 083 168 A | 3/2001 |
|---|---|---|
| EP | 1211242 A1 | 3/2001 |
| EP | 1 527 781 A1 | 5/2005 |
| JP | 2001-151749 A | 3/2001 |
| JP | 20011151749 * | 6/2001 |
| JP | 2002-161082 A | 6/2002 |
| WO | WO 99/61419 A1 | 12/1999 |
| WO | 01/19790 * | 3/2001 |

OTHER PUBLICATIONS

Proc. Natl. Acad. Sci. USA, vol. 85, pp. 4082-4086, 1988.
Hirotaka Onoe, et al. "Prostaglandin $D_2$, a cerebral sleep-inducing substance in monkeys" *Proc. Natl. Acad. Sci.* vol. 85, pp. 4082-4086, Jun. 1988.

* cited by examiner

*Primary Examiner*—Peter G O'Sullivan
(74) *Attorney, Agent, or Firm*—Sughrue Mion, PLLC

(57) ABSTRACT

A prostaglandin derivative represented by Formula (I):

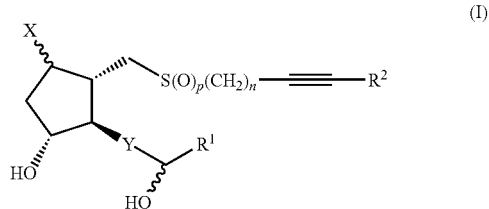

wherein X is a halogen atom in the α- or β-substitution, Y is an ethylene group, a vinylene group or an ethynylene group, $R^1$ is a $C_{3-10}$ cycloalkyl group, a $C_{3-10}$ cycloalkyl group substituted with a $C_{1-4}$ straight or branched chain alkyl group or a $C_{4-13}$ cycloalkylalkyl group, $R^2$ is a hydrogen atom or a $CO_2R^3$ group ($R^3$ is a hydrogen atom, a $C_{1-4}$ straight or branched chain alkyl group or a $C_{2-4}$ straight or branched chain alkenyl group), n is an integer of 1 to 4 and p is 0, 1 or 2,
a pharmaceutically acceptable salt thereof or a hydrate thereof.

3 Claims, No Drawings

PROSTAGLANDIN DERIVATIVES

This is a National Stage of Application No. PCT/JP2003/008864 filed Jul. 11, 2003.

TECHNICAL FIELD

The present invention relates to a novel prostaglandin derivative, a pharmaceutically acceptable salt thereof or a hydrate thereof and a sleep-inducing agent containing the same as the effective ingredient.

BACKGROUND ART

Since prostaglandins (hereinafter referred to as "PG(s)") exhibit various important physiological actions in trace amounts, the syntheses of natural PGs and a great number of their derivatives as well as their biological activities have been investigated with the intention of practical use as medicines, and have been reported in many types of literature.

Particularly, while various central nervous actions of PGs have been reported, their intracerebral contents, biosynthesis, metabolic pathways, intracerebral localizations and changes with growth or aging have been revealed. Interest has been maintained on their relations with sleep or arousal by PGs. Particularly, $PGD_2$ has been known as an intracerebral humoral factor that regulates the occurrence or maintenance of sleep; and it became clear that the sleep induced by $PGD_2$ in monkeys is indistinguishable from their spontaneous natural sleep in brain wave or behavior (Proc. Natl. Acad. Sci. USA, Vol. 85, pp. 4082-4086, 1988). $PGD_2$ was, therefore, expected to be a new compound possessing sleep-inducing action. However, $PGD_2$ derivatives including $PGD_2$ have not been put in practical use because of problems on their brain penetration and stability.

WO99/61419 discloses a compound having an ethynylene group at its α-chain. This compound is difficult to crystallize and presents the problem of formulation.

DISCLOSURE OF THE INVENTION

An object of the present invention is to provide PG derivatives possessing an excellent sleep-inducing action.

As a result of continued extensive studies, the present inventors found that prostaglandin derivatives represented by Formula (I) described below posses the excellent sleep-inducing action, upon which the present invention has been accomplished.

Specifically, according to one embodiment of the present invention, the invention is directed to a prostaglandin derivative represented by Formula (I):

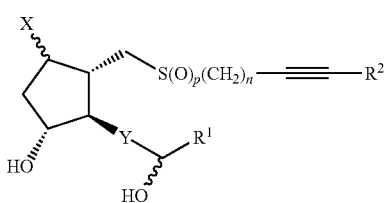

(I)

wherein X is a halogen atom in the α- or β-substitution, Y is an ethylene group, a vinylene group or an ethynylene group, $R^1$ is a $C_{3-10}$ cycloalkyl group, a $C_{3-10}$ cycloalkyl group substituted with a $C_{1-4}$ straight or branched chain alkyl group or a $C_{4-13}$ cycloalkylalkyl group, $R^2$ is a hydrogen atom or a $CO_2R^3$ group ($R^3$ is a hydrogen atom, a $C_{1-4}$ straight or branched chain alkyl group, or a $C_{2-4}$ straight or branched chain alkenyl group), n is an integer of 1 to 4 and p is 0, 1 or 2, a pharmaceutically acceptable salt thereof or a hydrate thereof.

According to another embodiment of the present invention, the invention is directed to a prostaglandin derivative represented by Formula (I) as described above wherein $R^1$ is a $C_{3-10}$ cycloalkyl group or a $C_{4-13}$ cycloalkylalkyl group, a pharmaceutically acceptable salt thereof or a hydrate thereof.

According to a further embodiment of the present invention, the invention is directed to a prostaglandin derivative represented by Formula (I) as described above wherein X is a chlorine atom or a bromine atom in the α- or β-substitution, a pharmaceutically acceptable salt thereof or a hydrate thereof.

According to a still further embodiment of the present invention, the invention is directed to a prostaglandin derivative represented by Formula (I) as described above wherein Y is an ethynylene group, a pharmaceutically acceptable salt thereof or a hydrate thereof.

According to a still further embodiment of the present invention, the invention is directed to a prostaglandin derivative represented by Formula (I) as described above wherein $R^2$ is a $CO_2R^3$ group, a pharmaceutically acceptable salt thereof or a hydrate thereof.

According to a still further embodiment of the present invention, the invention is directed to a prostaglandin derivative represented by Formula (I) as described above wherein p=0, a pharmaceutically acceptable salt thereof or a hydrate thereof.

According to a still further embodiment of the present invention, the invention is directed to a prostaglandin derivative represented by Formula (I) as described above wherein n=1 or 2, a pharmaceutically acceptable salt thereof or a hydrate thereof.

According to a still further embodiment of the present invention, the invention is directed to a pharmaceutical composition comprising the aforementioned prostaglandin derivative, a pharmaceutically acceptable salt thereof or a hydrate thereof.

BEST MODE FOR CARRYING OUT THE INVENTION

In the present invention, the halogen atom refers to a fluorine atom, a chlorine atom, a bromine atom or an iodine atom.

Examples of the $C_{3-10}$ cycloalkyl group include a cyclopropyl group, a cyclobutyl group, a cyclopentyl group, a cyclohexyl group, a cycloheptyl group and a cyclooctyl group.

Examples of the $C_{3-10}$ cycloalkyl group substituted with a $C_{1-4}$ straight or branched chain alkyl group include a methylcyclopropyl group, a methylcyclohexyl group, an ethylcyclohexyl group.

The $C_{4-13}$ cycloalkylalkyl group refers to an alkyl group substituted with a cycloalkyl group, and preferably a $C_{3-10}$ cycloalkyl-$C_{1-3}$ alkyl group. The examples include a cyclopropylmethyl group, a cyclobutylmethyl group, a cyclopentylmethyl group, a cyclopentylethyl group, a cyclohexylmethyl group, a cyclohexylethyl group and a cycloheptylmethyl group.

Examples of the $C_{1-4}$ straight or branched chain alkyl group include a methyl group, an ethyl group, a propyl group, an isopropyl group, a butyl group, an isobutyl group and a tert-butyl group.

Examples of the $C_{2-4}$ straight or branched chain alkenyl group include an allyl group, a crotyl group and a 2-methyl-2-propenyl group.

Examples of the pharmaceutically acceptable salts include salts with alkali metals (e.g., sodium and potassium), salts with alkaline earth metals (e.g., calcium and magnesium), ammonia, methylamine, dimethylamine, cyclopentylamine, benzylamine, piperidine, monoethanolamine, diethanolamine, monomethylmonoethanolamine, tromethamine, lysine and tris(hydroxymethyl)aminomethane.

Although n represents an integer of from 1 to 4, n=1 or n=2 is preferable in terms of crystallinity.

The compounds of Formula (I) may be prepared, for example, by the methods summarized in the following reaction schemes:

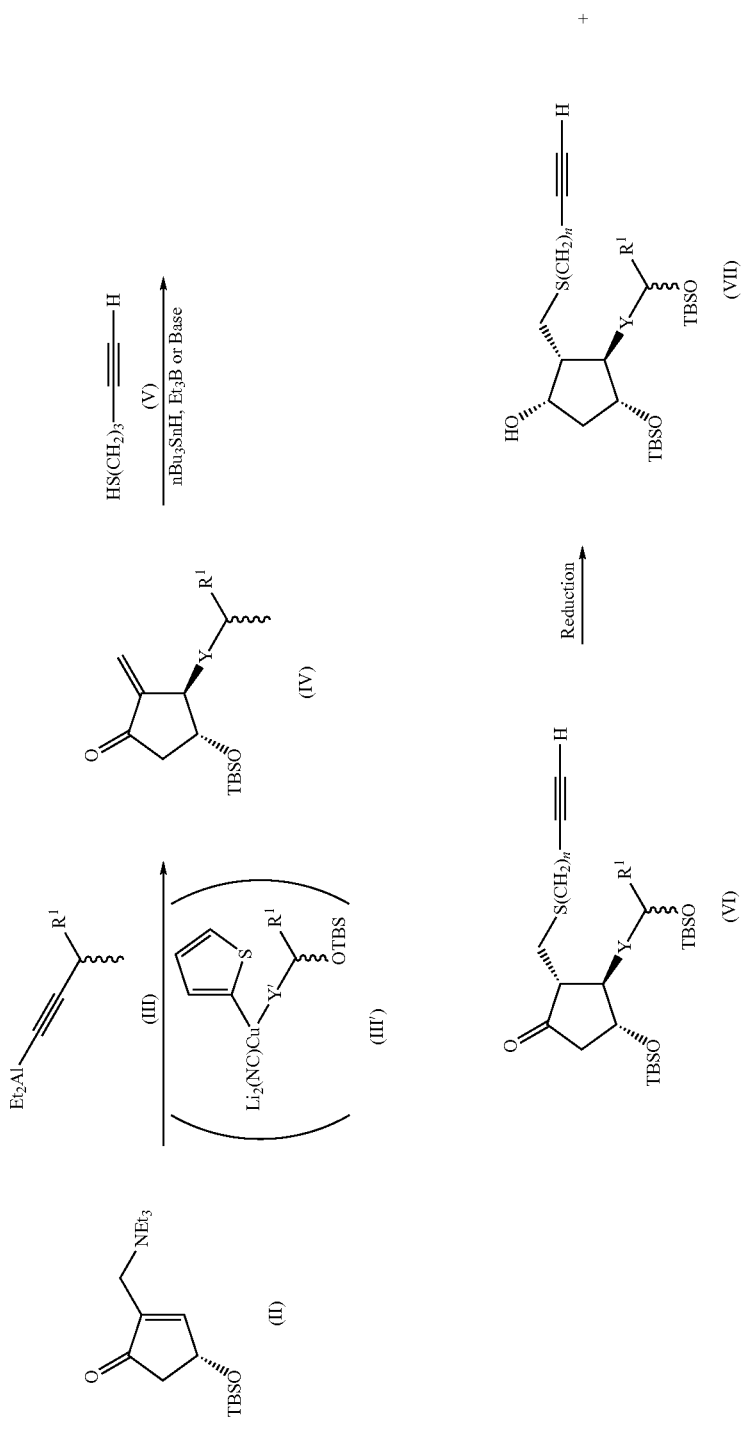

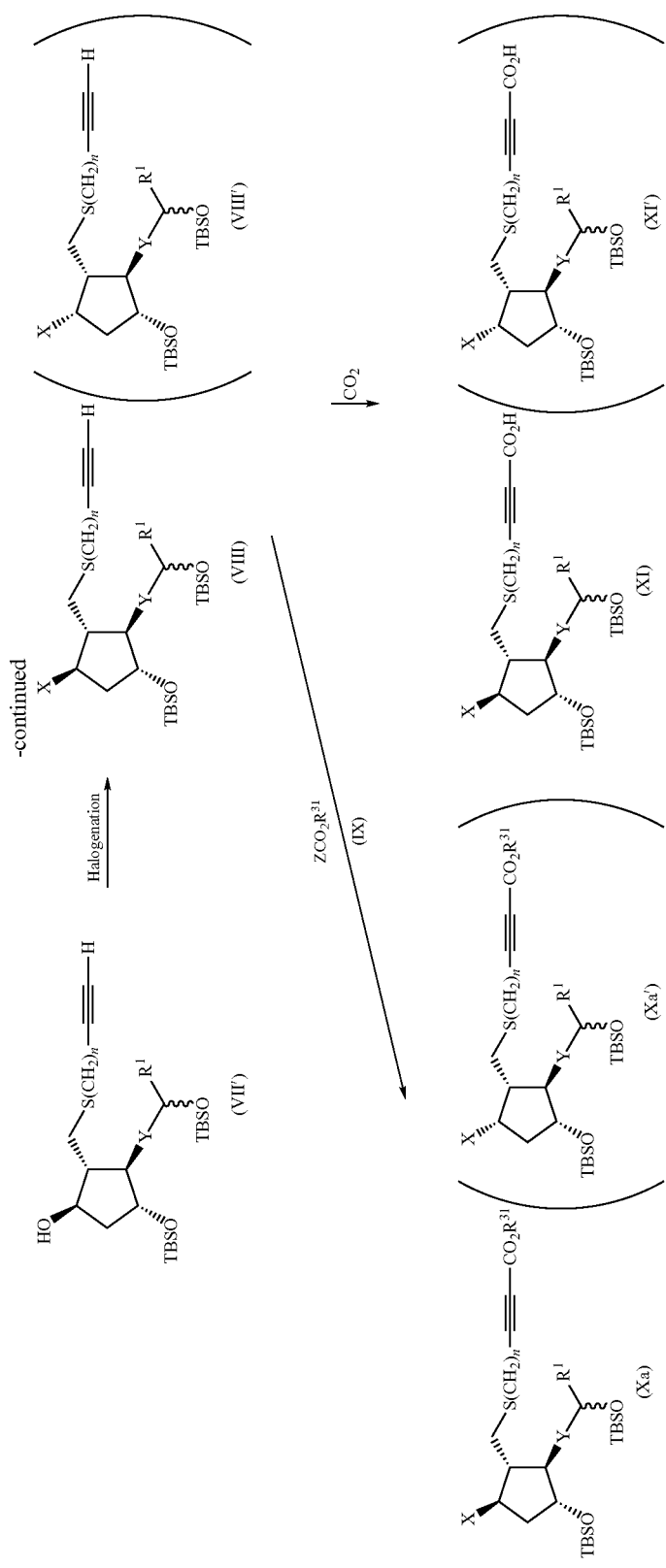

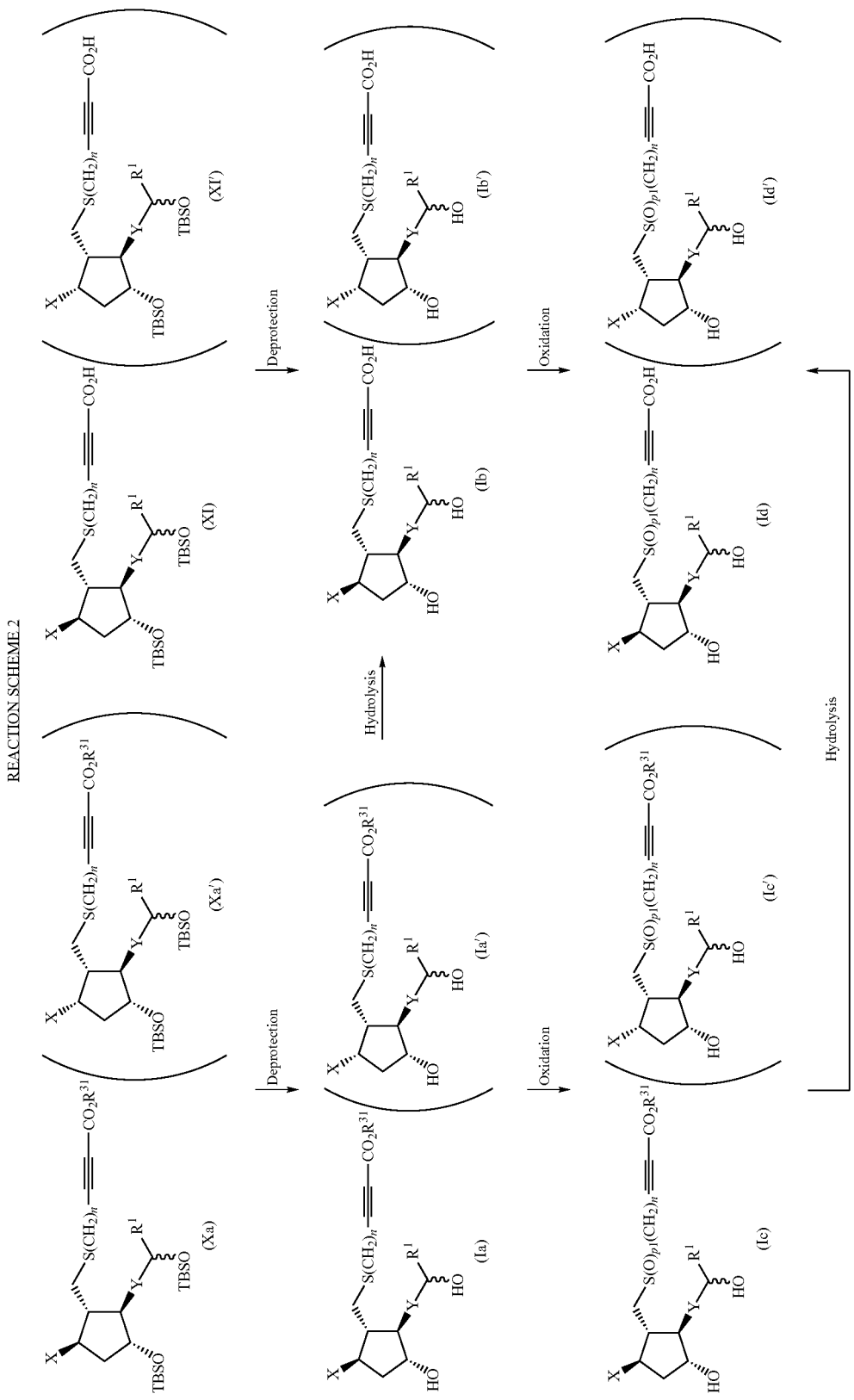

In the reaction schemes, TBS is a tert-butyldimethylsilyl group, Y' is an ethylene group or a vinylene group, $R^{31}$ is a $C_{1-4}$ alkyl group or a $C_{2-4}$ alkenyl group, p1 is 1 or 2, Z is a halogen atom and X, Y, $R^1$ and n are as previously defined.

The aforementioned reaction schemes are illustrated below.

(1) At first, the known compound of Formula (II) is reacted with 0.8 to 2.0 equivalents of a compound represented by Formula (III) or (III') in an inert solvent (e.g., benzene, toluene, tetrahydrofuran, diethyl ether, methylene chloride or n-hexane) at −78 to 30° C. according to the method of Sato et al. (Journal of Organic Chemistry, Vol. 53, p. 5590 (1988)) to stereospecifically give a compound of Formula (IV). Here, the compound wherein Y is an ethylene group or a vinylene group (i.e., the compound wherein Y is Y') can be obtained by a reaction using a compound of Formula (III') at −78 to 0° C., and the compound wherein Y is an ethynylene group can be obtained by a reaction using a compound of Formula (III) at 0 to 30° C.

(2) The compound of Formula (IV) is reacted with 1 to 6 equivalents of a compound represented by Formula (V) and 0.05 to 2 equivalents of a radical generating agent (e.g., azobisisobutyronitrile, azobiscyclohexanecarbonitrile, benzoyl peroxide or triethyl borane), if necessary, further with 1 to 5 equivalents of a radical reducing agent (e.g., tributyltin hydride, triphenyltin hydride, dibutyltin hydride or diphenyltin hydride) in an organic solvent (e.g., benzene, toluene, xylene, n-hexane, n-pentane or acetone) at −78 to 100° C. to give a compound of Formula (VI). Depending on the situation, the compound of Formula (VI) can also be obtained by a reaction using 0.05 to 2 equivalents of a base (e.g., an organic amine such as triethylamine, diisopropylamine, pyridine or dimethylaniline, or a base resin such as polyvinylpyrrolidone, diisopropylaminomethyl-polystyrene or (piperidinomethyl)polystyrene) in an organic solvent (e.g., benzene, toluene, xylene, n-hexane, n-pentane or acetone) at −78 to 100° C.

(3) The compound of Formula (VI) is reacted with 0.5 to 5 equivalents of a reducing agent (e.g., potassium borohydride, sodium borohydride, sodium cyanoborohydride, lithium tri-sec-butylborohydride or diisobutylaluminum hydride-BHT (2,6-di-tert-butyl-p-cresol)) in an organic solvent (e.g., tetrahydrofuran, diethyl ether, ethyl alcohol or methyl alcohol or toluene) at −78 to 40° C. to give compounds of Formula (VII) and (VII'). These compounds of Formula (VII) and (VII') can be purified by a conventional separation method such as column chromatography.

(4) The compound of Formula (VII) or Formula (VII') is mesylated or tosylated, for example, with 1 to 6 equivalents of methanesulfonyl chloride or p-toluenesulfonyl chloride in a suitable solvent such as pyridine, if necessary, in the presence of 0.8 to 6 equivalents of 4-dimethylaminopyridine at −20 to 40° C., followed by chlorination with 1 to 16 equivalents of tetra-n-butylammonium chloride to give a compound of Formula (VIII) or (VIII') wherein X is a chlorine atom. Here, bromination or fluorination can also be carried out in an ordinary manner. For example, bromination can be carried out by a reaction using 1 to 10 equivalents of carbon tetrabromide in the presence of 1 to 10 equivalents of triphenylphosphine and 1 to 10 equivalents of pyridine in acetonitrile. Fluorination can be carried out, for example, by a reaction with 5 to 20 equivalents of diethylaminosulfur trifluoride (DAST).

(5) The compound of Formula (VIII) or Formula (VIII') is reacted with a base (e.g., an alkyllithium such as n-butyllithium) in a suitable inert solvent (e.g., tetrahydrofuran or diethyl ether) at from −78° C. to room temperature, followed by reaction with a compound of Formula (IX) at from −78 to 40° C. to give a compound of Formula (Xa) or Formula (Xa'). Reaction with carbon dioxide instead of the compound of Formula (IX) can yield a compound of Formula (XI) or Formula (XI').

(6) The protecting group of a hydroxyl group of the compound of Formula (Xa) or Formula (Xa'), i.e., the tert-butyldimethylsilyl group is removed by using hydrofluoric acid, pyridium poly(hydrogenfluoride) or hydrochloric acid under conventional conditions in methanol, ethanol, acetonitrile or a mixed solvent of these, or a mixed solvent of the foregoing with water to give a PG derivative of Formula (Ia) or Formula (Ia').

(7) The compound of Formula (Ia) or Formula (Ia') is hydrolyzed by a reaction with an enzyme in a buffer solution such as phosphate buffer or Tris-hydrochloride buffer, if necessary, by using an organic solvent (e.g., a water-miscible solvent such as acetone, methanol or ethanol) to give a PG derivative of Formula (Ib) or (Ib') according to the present invention. For the enzyme, there are mentioned enzymes produced by microorganisms (e.g., those produced by the microorganisms belonging to *Candida* sp. or *Pseudomonas* sp.) and enzymes prepared from animal organs (e.g., pig liver or pig pancreas). Examples of the commercially available enzymes include lipase VII (derived from a microorganism belonging to *Candida* sp.: Sigma Co., Ltd.), lipase AY (derived from a microorganism belonging to *Candida* sp.: Amano Pharmaceutical Co., Ltd.), lipase PS (derived from a microorganism belonging to *Pseudomonas* sp.: Amano Pharmaceutical Co., Ltd.), lipase MF (derived from a microorganism belonging to *Pseudomonas* sp.: Amano Pharmaceutical Co., Ltd.), PLE (prepared from pig liver: Sigma Co., Ltd.), lipase II (prepared from pig pancreas: Sigma Co., Ltd.) and lipoprotein lipase (prepared from pig pancreas: Tokyo Kasei Kogyo Co., Ltd.).

The amount of the enzyme to be used may appropriately be determined, depending on the potency of the enzyme and the amount of the substrate (the compound of Formula (Ia) or (Ia')). It is usually 0.1 to 20 parts by weight based on the substrate. The reaction temperature is from 25 to 50° C., preferably 30 to 40° C.

Alternatively, the compound of Formula (Ia) or (Ia') is hydrolyzed using a base in a solvent ordinarily used for hydrolysis to give the PG derivative of Formula (Ib) or (Ib') according to the present invention. Examples of the base to be used here are lithium hydroxide and potassium carbonate. Examples of the solvent are acetonitrile, acetone, methanol, ethanol, water and a mixture of any of the foregoing.

The compound of Formula (XI) or (XI') is deprotected similarly to the above (6) to give the PG derivative of Formula (Ib) or (Ib') according to the present invention.

(8) The compound of Formula (Ia) or (Ia') is reacted with an oxidizing agent such as sodium metaperiodate, hydrogen peroxide, peracetic acid, m-chloroperbenzoic acid or tert-butyl hydroxyperoxide in diethyl ether, methanol, ethanol, methylene chloride, water or a mixture of any of the foregoing at from −20 to 50° C. to give a PG derivative of Formula (Ic) or (Ic').

(9) The compound of Formula (Ic) or (Ic') is hydrolyzed similarly to the above (7) to give a PG derivative of Formula (Id) or (Id') according to the present invention. In addition, the compound of Formula (Ib) or (Ib') is used and oxidized similarly to the above (8) to give the PG derivative of Formula (Id) or (Id').

$S(O)_p$ in the α-chain represents the formulae:

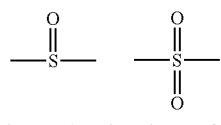

when p = 1; and   when p = 2

Representative compounds of Formula (I) according to the present invention are illustrated below.

TABLE 1

| Compound | X | Y | n | p | R¹ | R² | 15-position*⁾ |
|---|---|---|---|---|---|---|---|
| 1 | β-Cl | CH₂CH₂ | 2 | 0 | cyclopentyl | CO₂Me | α |
| 2 | β-Cl | CH₂CH₂ | 2 | 0 | cyclohexyl | CO₂H | α |
| 3 | α-Cl | CH₂CH₂ | 2 | 0 | cyclohexyl | H | α |
| 4 | β-Br | CH₂CH₂ | 3 | 0 | 4-methylcyclohexyl | CO₂H | α |
| 5 | β-Br | CH₂CH₂ | 1 | 1 | cycloheptyl | CO₂-allyl | α |
| 6 | β-Cl | (E) CH=CH | 2 | 0 | cyclopentylmethyl | CO₂Et | α |
| 7 | β-Cl | (E) CH=CH | 3 | 0 | cyclohexyl | CO₂H | β |
| 8 | F | (E) CH=CH | 2 | 0 | cyclohexylethyl | CO₂-tBu | α |
| 9 | β-Br | (E) CH=CH | 4 | 2 | cyclooctyl | CO₂H | α |
| 10 | β-Cl | (Z) CH=CH | 2 | 0 | cyclopentylmethyl | CO₂H | α |
| 11 | β-Cl | C≡C | 2 | 0 | cyclopentyl | CO₂H | α |
| 12 | β-Cl | C≡C | 2 | 0 | cyclohexyl | H | α |
| 13 | β-Cl | C≡C | 1 | 0 | cyclohexyl | CO₂Me | α |
| 14 | β-Cl | C≡C | 1 | 0 | cyclohexyl | CO₂H | α |
| 15 | α-Cl | C≡C | 1 | 0 | cyclohexyl | CO₂H | α |
| 16 | β-Cl | C≡C | 2 | 0 | cyclohexyl | CO₂H | α |
| 17 | β-Br | C≡C | 2 | 0 | cyclohexyl | CO₂H | α |
| 18 | F | C≡C | 2 | 0 | cyclohexyl | CO₂H | α |
| 19 | β-Cl | C≡C | 3 | 0 | cyclohexyl | CO₂Me | α |
| 20 | α-Br | C≡C | 3 | 0 | cyclohexyl | CO₂Me | β |
| 21 | F | C≡C | 3 | 0 | cyclohexyl | CO₂Me | α |
| 22 | β-Cl | C≡C | 3 | 0 | cyclohexyl | CO₂H | α |
| 23 | β-Cl | C≡C | 2 | 0 | cyclohexylmethyl | CO₂H | α |
| 24 | β-Cl | C≡C | 2 | 0 | cycloheptyl | CO₂H | α |
| 25 | β-Cl | C≡C | 2 | 0 | cyclooctyl | CO₂H | α |

(E) CH=CH: trans-vinylene,
(Z) CH=CH: cis-vinylene,
*⁾Bonding between the carbon atom adjacent to R¹ and the OH group The compounds of the present invention can be administered systemically or topically, or orally or parenterally such as intravenously or nasally. They can be, for example, administered orally in the form of tablets, dusting powders, granules, powders, capsules, solutions, emulsions, suspensions or the like, any of which may be prepared according to conventional methods. As the dosage forms for intravenous administration, there are used aqueous or non-aqueous solutions, emulsions, suspensions or solid preparations to be dissolved in solvents for injection immediately before use. Nasal administration can be performed by quantitatively spraying a solution or a powder (hard capsule) containing the drug into the nasal cavity by the use of a dedicated nasal dropper or sprayer. Further, the compounds of the present invention can be formulated into the forms of inclusion compounds with α-, β-, or γ-cyclodextrin or methylated cyclodextrin. In addition, the compounds of the present invention can be administered by injection in the form of aqueous or non-aqueous solutions, emulsions, suspensions or the like. Although the dose may be varied according to the age, body weight, etc., it is from 1 ng to 1 mg/day per adult and may be administered once a day or several times a day in divided doses.

The present invention will be described in more details by way of the following test example and examples, but the invention is in no way limited to the descriptions of these examples.

Test Example

Sleep-Inducing Test by Cisternal Administration

Method:

Four male cynomolgus monkeys weighing 2.0-3.5 kg were individually placed in cages. The behaviors of the respective animals were recorded by videotape from one hour before drug administration to three hours after drug administration. Compound 16 was dissolved in physiological saline solution and sterilized using a Minipore filter. The drug was cisternally infused into the monkeys anesthetized with isoflurane inhalation. The dose was 10 μg/0.1 ml per monkey and 100 μg/0.1 ml per monkey. The same dose of the vehicle was infused cisternally to the control group. The test schedule was carried out according to the following protocol.

Week 1: Group treated with vehicle
Week 2: Group treated with 10 μg of Compound 16/monkey
Week 3: Group treated with 100 μg of Compound 16/monkey The sleep times at three hours after administration were determined by playing back the recorded videotape and measuring the times (second) during which the animals relaxed with their both eyes closed, which are shown in Table 2.

TABLE 2

|  | Sleep time (sec) | Number of slept animals |
|---|---|---|
| Vehicle-treated group | 0 | 0/4 |
| 10 μg/monkey treated group | 293 | 3/4 |

TABLE 2-continued

|  | Sleep time (sec) | Number of slept animals |
|---|---|---|
| 100 μg/monkey treated group | 1734 | 4/4 |

Example 1

9-Deoxy-9β-chloro-16,17,18,19,20-pentanor-15-cyclohexyl-2,2,3,3,13,14-hexadehydro-6-thia-PGF$_1$α (Compound 16)

(1) (3S)-3-(tert-Butyldimethylsiloxy)-3-cyclohexylprop-1-yne (6.58 g) was dissolved in toluene (80 ml), and n-butyl lithium (3.0 M, hexane solution, 8.0 ml) was added at 0° C., followed by stirring at the same temperature for 30 minutes. To the solution was added diethylaluminum chloride (0.95 M, hexane solution 29.0 ml) at 0° C., followed by stirring until the solution reached room temperature for 30 minutes. To the solution was added (4R)-2-(N,N-diethylamino)methyl-4-(tert-butyldimethylsiloxy)-cyclopent-2-en-1-one (0.25 M, toluene solution, 80.0 ml) at room temperature, followed by stirring for 15 minutes. The reaction solution, while stirring, was added to a mixture of hexane (190 ml), a saturated aqueous ammonium chloride solution (190 ml) and an aqueous hydrochloric acid solution (3 M, 56 ml), and the organic layer was separated and washed with a saturated aqueous sodium bicarbonate solution (50 ml). The resulting organic layer was dried over anhydrous magnesium sulfate, filtered and concentrated. The resulting residue was purified by silica gel column chromatography (developing solvent; hexane:ether=10:1) to give (3R,4R)-2-methylene-3-[(3S)-3-(tert-butyldimethylsiloxy)-3-cyclohexylprop-1-ynyl]-4-(tert-butyldimethylsiloxy)cyclopentan-1-one (7.92 g).

$^1$H-NMR (CDCl$_3$, 200 MHz) δ ppm: 0.07, 0.08, 0.12 (3s, 12H), 0.88 (s, 18H), 0.92-1.92 (m, 11H), 2.32 (dd, J=17.8, 7.4 Hz, 1H), 2.71 (dd, J=17.8, 6.5 Hz, 1H), 3.48-3.58 (m, 1H), 4.11 (dd, J=6.2, 1.4 Hz, 1H), 4.20-4.32 (m, 1H), 5.55 (d, J=2.6 Hz, 1H), 6.13 (d, J=3.0 Hz, 1H).

IR (neat): 2930, 2850, 1735, 1640, 1470, 1380, 1255, 830, 770 cm$^{-1}$.

(2) A toluene solution (6 ml) of the compound obtained in the above (1) (2.63 g) and 4-mercapto-1-butyn (4.63 g, 9.8% xylene solution) was stirred at room temperature for 3 days. The reaction solution was concentrated under reduced pressure, and then the resulting residue was purified by silica gel column chromatography (developing solvent; n-hexane:ethyl acetate=40:1) to give 2-decarboxy-16,17,18,19,20-pentanor-15-cyclohexyl-2,2,3,3,13,14-hexahydro-6-thia-PGE$_1$ 11,15-bis(tert-butyldimethylsilyl ether) (1.52 g).

$^1$H-NMR (CDCl$_3$, 300 MHz) δ ppm: 0.08 (s, 3H), 0.09 (s, 3H), 0.10 (s, 3H), 0.13 (s, 3H), 0.82-1.92 (m, 11H), 0.89 (s, 9H), 0.90 (s, 9H), 2.02 (t, J=2.6 Hz, 1H), 2.17-2.55 (m, 4H), 2.67-2.81 (m, 1H), 2.71 (t, J=7.2 Hz, 2H), 2.91 (d, J=5.9 Hz, 1H), 3.08-3.19 (m, 1H), 4.09 (dd, J=6.2, 1.7 Hz, 1H), 4.30-4.39 (m, 1H).

IR (neat): 3312, 2929, 2856, 1750, 1472, 1463, 1451, 1362, 1252, 1105, 1064, 1006, 940, 898, 837, 778, 669, 637 cm$^{-1}$ (3) To a toluene solution (6.3 ml) of BHT (2,6-di-tert-butyl-p-cresol) (1.13 g) was added dropwise diisobutylaluminum hydride (0.9 M, hexane solution, 5.2 ml) at −78° C., followed by stirring at −10° C. for 1 hour. To the solution was added dropwise a toluene solution (21.3 ml) of the compound obtained in the above (2) (1.20 g), followed by stirring at −25° C. for 1 hour. Saturated ammonium chloride solution was added to the reaction solution and the solution was made weakly acidic with a 1 M aqueous hydrochloric acid solution, followed by extraction with ethyl acetate. The organic layer was washed with a 1 M aqueous hydrochloric acid solution and a saturated aqueous sodium chloride solution, dried over anhydrous magnesium sulfate and filtered. The filtrate was concentrated under reduced pressure, and then the resulting residue was purified by silica gel column chromatography (developing solvent; n-hexane:ethyl acetate=20:1 to 5:1) to give 2-decarboxy-16,17,18,19,20-pentanor-15-cyclohexyl-2,2,3,3,13,14-hexadehydro-6-thia-PGF$_1$α 11,15-bis(tert-butyldimethylsilyl ether) (930 mg) and 2-decarboxy-16,17,18,19,20-pentanor-15-cyclohexyl-2,2,3,3,13,14-hexadehydro-6-thia-PGF$_1$β 11,15-bis(tert-butyldimethylsilyl ether) (38 mg).

2-Decarboxy-16,17,18,19,20-pentanor-15-cyclohexyl-2,2,3,3,13,14-hexadehydro-6-thia-PGF$_1$α 11,15-bis(tert-butyldimethylsilyl ether)

$^1$H-NMR (CDCl$_3$, 300 MHz) δ ppm: 0.08 (s, 3H), 0.09 (s, 3H), 0.10 (s, 6H), 0.80-2.18 (m, 14H), 0.88 (s, 9H), 0.90 (s, 9H), 2.03 (t, J=2.6 Hz, 1H), 2.46-2.61 (m, 2H), 2.51 (dt, J=2.6, 7.5 Hz, 2H), 2.66-2.92 (m, 4H), 4.08 (dd, J=6.2, 1.7 Hz, 1H), 4.17-4.32 (m, 2H).

IR (neat): 3468, 3313, 2929, 2856, 2232, 2120, 1472, 1463, 1451, 1388, 1362, 1338, 1253, 1101, 1062, 1006, 964, 898, 837, 778, 668, 637 cm$^{-1}$.

2-Decarboxy-16,17,18,19,20-pentanor-15-cyclohexyl-2,2,3,3,13,14-hexadehydro-6-thia-PGF$_1$β 11,15-bis(tert-butyldimethylsilyl ether)

$^1$H-NMR (CDCl$_3$, 300 MHz) δ ppm: 0.07 (s, 3H), 0.08 (s, 6H), 0.11 (s, 3H), 0.76-2.07 (m, 14H), 0.88 (s, 9H), 0.90 (s, 9H), 2.05 (t, J=2.6 Hz, 1H), 2.34 (ddd, J=10.7, 6.4, 1.7 Hz, 1H), 2.41-2.59 (m, 4H), 2.71-2.79 (m, 2H), 3.05 (dd, J=13.4, 4.3 Hz, 1H), 4.03-4.28 (m, 2H), 4.08 (dd, J=6.1, 1.7 Hz, 1H).

IR (neat): 3436, 3313, 2929, 2856, 2234, 2121, 1472, 1463, 1451, 1388, 1362, 1338, 1252, 1101, 1066, 1006, 898, 837, 777, 669, 637 cm$^{-1}$ (4) To a pyridine solution (16 ml) of 2-decarboxy-16,17,18,19,20-pentanor-15-cyclohexyl-2,2,3,3,13,14-hexadehydro-6-thia-PGF$_1$α 11,15-bis(tert-butyldimethylsilyl ether) (925 mg) obtained in the above (3) was added methanesulfonyl chloride (0.253 ml) under an argon stream at 0° C., followed by stirring at room temperature for 3.5 hours. To the solution were added tetra-n-butyl ammonium chloride (3.64 g) and toluene (16 ml), followed by stirring at 45° C. overnight. After addition of water and hexane, the solution was made weakly acidic with a 6 M aqueous hydrochloric acid solution and extracted with n-hexane. The organic layer was washed with a saturated sodium chloride solution, dried over anhydrous magnesium sulfate and filtered. The filtrate was concentrated under reduced pressure and the resulting crude product was purified by silica gel column chromatography (developing solvent; n-hexane:ethyl acetate=20:1) to give 9-deoxy-9β-chloro-2-decarboxy-16,17,18,19,20-pentanor-15-cyclohexyl-2,2,3,3,13,14-hexadehydro-6-thia-PGF$_1$α 11,15-bis(tert-butyldimethylsilyl ether) (850 mg).

$^1$H-NMR (CDCl$_3$, 300 MHz) δ ppm: 0.07 (s, 3H), 0.08 (s, 3H), 0.09 (s, 3H), 0.11 (s, 3H), 0.78-1.90 (m, 11H), 0.88 (s, 9H), 0.90 (s, 9H), 2.03 (t, J=2.6 Hz, 1H), 2.11-2.37 (m, 3H), 2.50 (dt, J=2.6, 7.2 Hz, 2H), 2.57 (ddd, J=9.3, 5.4, 1.6 Hz, 1H), 2.74 (t, J=7.2 Hz, 2H), 2.87 (d, J=5.4 Hz, 2H), 4.09 (dd, J=6.1, 1.6 Hz, 1H), 4.13-4.33 (m, 2H).

IR (neat): 3313, 2953, 2929, 2856, 2234, 2121, 1472, 1463, 1451, 1387, 1362, 1339, 1281, 1253, 1155, 1101, 1006, 962, 927, 898, 837, 778, 668, 638 cm$^{-1}$.

(5) To a tetrahydrofuran solution (28.8 ml) of the compound (840 mg) obtained in the above (4) was added n-butyllithium (1.59 M, hexane solution, 0.95 ml) under an argon stream at −78° C., followed by stirring at the same temperature for 1.5 hours. Dry ice was added to the reaction solution and the solution was allowed to reach room temperature. The reaction was then poured to a saturated ammonium chloride solution and the solution was made weakly acidic with a 2 M aqueous hydrochloric acid solution and extracted with ethyl acetate. The organic layer was washed with a saturated sodium chloride solution, dried over anhydrous magnesium sulfate and filtered. The filtrate was concentrated under reduced pressure and the resulting residue was purified by silica gel column chromatography (developing solvent; n-hexane:ethyl acetate=10:1 to 1:2) to give 9-deoxy-9β-chloro-16,17,18,19,20-pentanor-15-cyclohexyl-2,2,3,3,13,14-hexahydro-6-thia-PGF$_1$α 11,15-bis(tert-butyldimethylsilyl ether) (728 mg).

$^1$H-NMR (CDCl$_3$, 300 MHz) δ ppm: 0.08 (s, 3H), 0.09 (2s, 6H), 0.11 (s, 3H), 0.74-1.92 (m, 12H), 0.88 (s, 9H), 0.90 (s, 9H), 2.13-2.36 (m, 3H), 2.55 (ddd, J=9.1, 5.2, 1.6 Hz, 1H), 2.59-2.83 (m, 4H), 2.88 (d, J=5.4 Hz, 2H), 4.05-4.32 (m, 2H), 4.09 (dd, J=6.3, 1.6 Hz, 1H).

IR (neat): 3400, 2929, 2856, 2241, 1691, 1472, 1464, 1451, 1411, 1385, 1362, 1279, 1255, 1156, 1087, 1006, 962, 898, 837, 778, 670, 590, 504 cm$^{-1}$ (6) To a methyl alcohol solution (22.8 ml) of the compound obtained in the above (5) (720 mg) was added conc. hydrochloric acid (0.114 ml) at room temperature, followed by stirring for 4 hours. The reaction solution was added to a mixture of ethyl acetate and a saturated aqueous sodium bicarbonate solution, and the organic layer was separated. The aqueous layer was extracted with ethyl acetate, and the organic layers were combined, washed with a saturated aqueous sodium bicarbonate solution, dried over anhydrous magnesium sulfate and filtered. The filtrate was concentrated under reduced pressure and the resulting crude product was purified by silica gel column chromatography (developing solvent; chloroform:methanol=20:1) to give the title compound (312 mg).

$^1$H-NMR (CDCl$_3$, 300 MHz) δ ppm: 0.84-1.90 (m, 11H), 2.20-2.44 (m, 3H), 2.59-3.50 (m, 8H), 2.90 (dd, J=13.6, 5.0 Hz, 1H), 2.97 (dd, J=13.6, 5.5 Hz, 1H), 4.07-4.23 (m, 2H), 4.35-4.45 (m, 1H).

IR (neat): 3368, 2928, 2853, 2624, 2239, 1696, 1450, 1417, 1278, 1156, 1082, 1005, 893, 828, 795, 755, 592 cm$^{-1}$.

m.p. 77-78° C.

Example 2

9-Deoxy-9β-chloro-2-decarboxy-16,17,18,19,20-pentanor-15-cyclohexyl-2,2,3,3,13,14-hexahydro-6-thia-PGF$_1$α (Compound 12)

Following the substantially same manner as in Example 1(6) but using the compound (112 mg) obtained in Example 1(4), the title compound was obtained.

$^1$H-NMR (CDCl$_3$, 300 MHz) δ ppm: 0.82-2.98 (m, 16H), 2.05 (t, J=2.6 Hz, 1H), 2.51 (dt, J=2.6, 7.2 Hz, 2H), 2.61 (ddd, J=10.1, 6.6, 1.9 Hz, 1H), 2.76 (t, J=7.2 Hz, 2H), 2.87 (dd, J=13.8, 5.0 Hz, 1H), 2.93 (dd, J=13.8, 5.1 Hz, 1H), 4.07-4.25 (m, 2H), 4.34-4.45 (m, 1H).

IR (neat): 3368, 3304, 2926, 2852, 2236, 2118, 1450, 1384, 1284, 1228, 1153, 1083, 1008, 893, 832, 641 cm$^{-1}$.

Example 3

9-Deoxy-9β-chloro-2,16,17,18,19,20-hexanor-15-cyclohexyl-3,3,4,4,13,14-hexahydro-6-thia-PGF$_1$α (Compound 14)

(1) Following the substantially same manner as in Example 1(2) but using 3-mercapto-1-propyne instead of 4-mercapto-1-butyne, 2-decarboxy-2,16,17,18,19,20-hexanor-15-cyclohexyl-3,3,4,4,13,14-hexahydro-6-thia-PGE$_1$ 11,15-bis(tert-butyldimethylsilyl ether) was obtained.

$^1$H-NMR (CDCl$_3$, 300 MHz) δ ppm: 0.08 (s, 3H), 0.09 (s, 3H), 0.10 (s, 3H), 0.13 (s, 3H), 0.80-1.90 (m, 11H), 0.89 (s, 9H), 0.90 (s, 9H), 2.24 (dd, J=18.0, 6.4 Hz, 1H), 2.25 (t, J=2.6 Hz, 1H), 2.50-2.60 (m, 1H), 2.73 (ddd, J=18.0, 6.3, 1.0 Hz, 1H), 2.99 (dd, J=13.7, 7.2 Hz, 1H), 3.08 (dd, J=13.7, 5.1 Hz, 1H), 3.08-3.16 (m, 1H), 3.27 (d, J=2.6 Hz, 2H), 4.08 (dd, J=6.4, 1.7 Hz, 1H), 4.32-4.40 (m, 1H).

IR (neat): 3311, 2929, 2856, 2236, 1750, 1472, 1386, 1362, 1253, 1106, 1065, 1006, 940, 898, 837, 778, 669 cm$^{-1}$.

(2) Following the substantially same manner as in Example 1(3) but using the compound obtained in the above (1), 2-decarboxy-2,16,17,18,19,20-hexanor-15-cyclohexyl-3,3,4,4,13,14-hexahydro-6-thia-PGF$_1$α 11,15-bis(tert-butyldimethylsilyl ether) and 2-decarboxy-2,16,17,18,19,20-hexanor-15-cyclohexyl-3,3,4,4,13,14-hexahydro-6-thia-PGF$_1$β 11,15-bis(tert-butyldimethylsilyl ether) were obtained.

2-Decarboxy-2,16,17,18,19,20-hexanor-15-cyclohexyl-3,3,4,4,13,14-hexahydro-6-thia-PGF$_1$α 11,15-bis(tert-butyldimethylsilyl ether)

$^1$H-NMR (CDCl$_3$, 300 MHz) δ ppm: 0.08 (s, 3H), 0.09 (s, 3H), 0.11 (s, 6H), 0.82-1.90 (m, 12H), 0.89 (s, 9H), 0.90 (s, 9H), 2.02-2.16 (m, 2H), 2.23 (t, J=2.6 Hz, 1H), 2.59-2.63 (m, 2H), 2.98 (d, J=7.8 Hz, 2H), 3.23-3.37 (m, 2H), 4.07 (dd, J=6.3, 1.8 Hz, 1H), 4.20-4.33 (m, 2H).

IR (neat): 3468, 3313, 2929, 2856, 2232, 1472, 1451, 1388, 1362, 1338, 1253, 1101, 1062, 1005, 926, 898, 837, 777, 668, 634 cm$^{-1}$.

2-Decarboxy-2,16,17,18,19,20-hexanor-15-cyclohexyl-3,3,4,4,13,14-hexahydro-6-thia-PGF$_1$β 11,15-bis(tert-butyldimethylsilyl ether)

$^1$H-NMR(CDCl$_3$, 300 MHz) δ ppm: 0.07 (s, 3H), 0.08 (s, 6H), 0.12 (s, 3H), 0.78-2.12 (m, 13H), 0.88 (s, 9H), 0.90 (s, 9H), 1.97 (t, J=6.6 Hz, 2H), 2.27 (t, J=2.0 Hz, 1H), 2.37 (ddd, J=9.6, 6.1, 1.5 Hz, 1H), 2.68 (dd, J=13.4, 9.7 Hz, 1H), 3.16 (dd, J=13.4, 4.5 Hz, 1H), 3.22-3.39 (m, 2H), 4.02-4.29 (m, 2H), 4.08 (dd, J=6.2, 1.5 Hz, 1H).

IR (neat): 3400, 3313, 2929, 2856, 2233, 1472, 1463, 1451, 1386, 1362, 1338, 1252, 1101, 1066, 1006, 898, 837, 777, 669, 636 cm$^{-1}$.

(3) Following the substantially same manner as in Example 1(4) but using 2-decarboxy-2,16,17,18,19,20-hexanor-15-cyclohexyl-3,3,4,4,13,14-hexahydro-6-thia-PGF$_1$α 11,15-bis(tert-butyldimethylsilyl ether), 9-deoxy-9β-chloro-2-decarboxy-2,16,17,18,19,20-hexanor-15-cyclohexyl-3,3,4,4,13,14-hexahydro-6-thia-PGF$_1$α 11,15-bis(tert-butyldimethylsilyl ether) was obtained.

$^1$H-NMR (CDCl$_3$, 300 MHz) δ ppm: 0.08 (2s, 6H), 0.09 (s, 3H), 0.12 (s, 3H), 0.82-1.90 (m, 11H), 0.88 (s, 9H), 0.90 (s, 9H), 2.14-2.29 (m, 2H), 2.26 (t, J=2.6 Hz, 1H), 2.31-2.43 (m, 1H), 2.56 (ddd, J=8.8, 4.9, 1.7 Hz, 1H), 2.95 (dd, J=13.6, 6.1 Hz, 1H), 3.02 (dd, J=13.6, 5.8 Hz, 1H), 3.31 (d, J=2.6 Hz, 2H), 4.08 (dd, J=6.2, 1.7 Hz, 1H), 4.12-4.32 (m, 2H).

IR (neat): 3313, 2952, 2929, 2856, 2234, 1472, 1464, 1451, 1408, 1389, 1362, 1253, 1100, 1006, 962, 927, 898, 837, 778, 668, 637 cm$^{-1}$.

(4) Following the substantially same manner as in Example 1(5) but using the compound obtained in the above (3), 9-deoxy-9β-chloro-2,16,17,18,19,20-hexanor-15-cyclohexyl-3,3,4,4,13,14-hexadehydro-6-thia-PGF$_1$α 11,15-bis(tert-butyldimethylsilyl ether) was obtained.

$^1$H-NMR (CDCl$_3$, 300 MHz) δ ppm: 0.08 (s, 3H), 0.09 (2s, 6H), 0.12 (s, 3H), 0.76-1.91 (m, 12H), 0.88 (s, 9H), 0.91 (s, 9H), 2.14-2.40 (m, 3H), 2.54 (ddd, J=9.1, 5.0, 1.5 Hz, 1H), 2.96 (dd, J=13.6, 5.8 Hz, 1H), 3.04 (dd, J=13.6, 5.4 Hz, 1H), 3.37-3.51 (m, 2H), 4.01-4.33 (m, 2H), 4.09 (dd, J=6.3, 1.5 Hz, 1H).

IR (neat): 2929, 2856, 2240, 1692, 1472, 1451, 1409, 1362, 1279, 1256, 1100, 1006, 962, 898, 837, 778, 670, 602 cm$^{-1}$.

(5) Following the substantially same manner as in Example 1(6) but using the compound obtained in the above (4), the titled compound was obtained.

$^1$H-NMR (CDCl$_3$, 300 MHz) δ ppm: 0.93-1.92 (m, 11H), 2.22-2.46 (m, 3H), 2.67-2.81 (m, 1H), 2.87-3.58 (m, 3H), 2.93 (dd, J=13.8, 4.8 Hz, 1H), 3.15 (dd, J=13.8, 5.4 Hz, 1H), 3.44 (s, 2H), 4.09-4.25 (m, 2H), 4.34-4.47 (m, 1H).

IR (KBr): 3402, 2929, 2854, 2239, 1694, 1576, 1451, 1380, 1275, 1162, 1083, 1007, 894, 880, 782, 758, 666, 588, 499, 471 cm$^{-1}$.

Example 4

1a-Homo-9-deoxy-9β-chloro-16,17,18,19,20-pentanor-15-cyclohexyl-1a,1a,2,2,13,14-hexadehydro-6-thia-PGF$_1$α methyl ester (Compound 19)

(1) Following the substantially same manner as in Example 1(2) but using 5-mercapto-1-pentyne instead of 4-mercapto-1-butyne, 1a-homo-1a-decarboxy-16,17,18,19,20-pentanor-15-cyclohexyl-1a,1a,2,2,13,14-hexadehydro-6-thia-PGE$_1$ 11,15-bis(tert-butyldimethylsilyl ether) was obtained.

$^1$H-NMR (CDCl$_3$, 300 MHz) δ ppm: 0.08 (s, 3H), 0.09 (s, 3H), 0.10 (s, 3H), 0.13 (s, 3H), 0.80-1.92 (m, 13H), 0.89 (s, 9H), 0.90 (s, 9H), 1.96 (t, J=2.6 Hz, 1H), 2.23 (dd, J=18.0, 5.8 Hz, 1H), 2.31 (dt, J=2.6, 7.0 Hz, 2H), 2.43-2.52 (m, 1H), 2.64 (t, J=7.2 Hz, 2H), 2.71 (dd, J=18.0, 7.3 Hz, 1H), 2.81-2.94 (m, 2H), 3.10-3.20 (m, 1H), 4.08 (dd, J=6.3, 1.6 Hz, 1H), 4.30-4.39 (m, 1H).

IR (neat): 3314, 2929, 2856, 2236, 1751, 1472, 1463, 1451, 1386, 1362, 1253, 1106, 1065, 1006, 940, 898, 837, 778, 669, 634 cm$^{-1}$.

(2) Following the substantially same manner as in Example 1(3) but using the compound obtained in the above (1), 1a-homo-1a-decarboxy-16,17,18,19,20-pentanor-15-cyclohexyl-1a,1a,2,2,13,14-hexadehydro-6-thia-PGF$_1$α 11,15-bis(tert-butyldimethylsilyl ether) and 1a-homo-1a-decarboxy-16,17,18,19,20-pentanor-15-cyclohexyl-1a,1a,2,2,13,14-hexahydro-6-thia-PGF$_1$β 11,15-bis(tert-butyldimethylsilyl ether) were obtained.

1a-Homo-1a-decarboxy-16,17,18,19,20-pentanor-15-cyclohexyl-1a,1a,2,2,13,14-hexadehydro-6-thia-PGF$_1$α 11,15-bis(tert-butyldimethylsilyl) ether $^1$H-NMR (CDCl$_3$, 300 MHz) δ ppm: 0.08 (s, 3H), 0.09 (s, 3H), 0.11 (s, 6H), 0.78-1.91 (m, 14H), 0.89 (s, 9H), 0.90 (s, 9H), 1.93-2.18 (m, 2H), 1.96 (t, J=2.6 Hz, 1H), 2.33 (dt, J=2.6, 6.9 Hz, 2H), 2.50-2.61 (m, 2H), 2.68 (t, J=7.1 Hz, 2H), 2.81 (d, J=7.6 Hz, 2H), 4.08 (dd, J=6.2, 1.6 Hz, 1H), 4.20-4.33 (m, 2H).

IR (neat): 3468, 3313, 2929, 2855, 2232, 1472, 1451, 1388, 1362, 1338, 1252, 1101, 1062, 1005, 918, 898, 837, 777, 668, 633 cm$^{-1}$.

1a-Homo-1a-decarboxy-16,17,18,19,20-pentanor-15-cyclohexyl-1a,1a,2,2,13,14-hexadehydro-6-thia-PGF$_1$β 11,15-bis(tert-butyldimethylsilyl ether)

$^1$H-NMR (CDCl$_3$, 300 MHz) δ ppm: 0.06 (s, 3H), 0.07 (s, 3H), 0.08 (s, 3H), 0.11 (s, 3H), 0.74-2.10 (m, 17H), 0.88 (s, 9H), 0.90 (s, 9H), 2.21-2.37 (m, 1H), 2.33 (dt, J=2.5 7.0 Hz, 2H), 2.47 (dd, J=13.3, 10.4 Hz, 1H), 2.53-2.63 (m, 1H), 2.69 (t, J=7.2 Hz, 2H), 3.00 (dd, J=13.3, 4.1 Hz, 1H), 4.00-4.28 (m, 2H), 4.08 (dd, J=6.1, 1.3 Hz, 1H).

IR (neat): 3400, 3314, 2929, 2856, 2232, 1472, 1463, 1451, 1385, 1362, 1253, 1101, 1067, 1006, 898, 836, 777, 669, 634 cm$^{-1}$.

(3) Following the substantially same manner as in Example 1(4) but using 1a-homo-1a-decarboxy-16,17,18,19,20-pentanor-15-cyclohexyl-1a,1a,2,2,13,14-hexadehydro-6-thia-PGF$_1$α 11,15-bis(tert-butyldimethylsilyl ether), 1a-homo-1a-decarboxy-9-deoxy-9β-chloro-16,17,18,19,20-pentanor-15-cyclohexyl-1a,1a,2,2,13,14-hexadehydro-6-thia-PGF$_1$α 11,15-bis(tert-butyldimethylsilyl ether) was obtained.

$^1$H-NMR (CDCl$_3$, 300 MHz) δ ppm: 0.08 (2s, 6H), 0.09 (s, 3H), 0.12 (s, 3H), 0.81-1.90 (m, 13H), 0.88 (s, 9H), 0.91 (s, 9H), 1.97 (t, J=2.6 Hz, 1H), 2.11-2.44 (m, 5H), 2.53-2.62 (m, 1H), 2.68 (t, J=7.1 Hz, 2H), 2.82 (d, J=5.4 Hz, 2H), 4.04-4.32 (m, 3H).

IR (neat): 3313, 2929, 2856, 2234, 1472, 1463, 1451, 1388, 1362, 1281, 1253, 1100, 1006, 962, 927, 898, 837, 778, 668, 635 cm$^{-1}$.

(4) To a tetrahydrofuran solution (3.3 ml) of the compound (395 mg) obtained in the above (3) was added n-butyllithium (1.59 M, hexane solution, 447 μl) at −78° C., followed by stirring at the same temperature for 1 hour. To the solution was then added dropwise a tetrahydrofuran solution (3.3 ml) of methyl chloroformate (75 mg) at the same temperature, followed by stirring at room temperature overnight. The reaction solution was poured into a saturated aqueous sodium chloride solution and the solution was made weakly acidic with a 1 M aqueous hydrochloric acid solution and extracted with n-hexane. The organic layer was washed with a saturated sodium chloride solution, dried over anhydrous magnesium sulfate and filtered. The filtrate was concentrated under reduced pressure to afford a crude product. To a methanol solution (8.0 ml) of the crude product was added conc. hydrochloric acid (0.04 ml) at room temperature, followed by stirring for 4 hours. The reaction solution was added to a mixture of ethyl acetate and saturated sodium bicarbonate solution and the organic layer was separated. The aqueous layer was extracted with ethyl acetate. The organic layers were combined, washed with a saturated aqueous sodium bicarbonate solution, dried over anhydrous magnesium sulfate and filtered. The filtrate was concentrated under reduced pressure and the resulting crude product was purified by silica gel column chromatography (developing solvent; n-hexane:ethyl acetate=1:1) to give the title compound (130 mg).

$^1$H-NMR (CDCl$_3$, 300 MHz) δ ppm: 0.95-1.39 (m, 6H), 1.46-2.00 (m, 9H), 2.18-2.44 (m, 3H), 2.46-2.56 (m, 2H), 2.62 (ddd, J=10.1, 6.5, 1.9 Hz, 1H), 2.65-2.76 (m, 2H), 2.80 (dd, J=13.7, 5.0 Hz, 1H), 2.88 (dd, J=13.7, 5.1 Hz, 1H), 3.77 (s, 3H), 4.06-4.27 (m, 2H), 4.34-4.45 (m, 1H).

IR (neat): 3368, 2928, 2853, 2237, 1716, 1435, 1384, 1326, 1257, 1154, 1078, 1011, 894, 832, 753 cm$^{-1}$.

Example 5

1a-Homo-9-deoxy-9β-chloro-16,17,18,19,20-pentanor-15-cyclohexyl-1a,1a,2,2,13,14-hexahydro-6-thia-PGF$_1$α (Compound 22)

To a water suspension (16 ml) of lipase PS (2.3 g) was added an acetone solution (4.8 ml) of the compound (100 mg) obtained in Example 4. To this were then added phosphate buffer (0.2 M, pH=7.0, 2.5 ml) and water (32 ml), followed by stirring at 30° C. overnight. After filtration, ammonium sulfate was added to the mixture for salting out and it was extracted with ethyl acetate. The organic layer washed with a saturated aqueous sodium chloride solution, dried over anhydrous magnesium sulfate and filtered. The filtrate was concentrated under reduced pressure and the resulting crude product was purified by silica gel column chromatography (developing solvent; ethyl acetate) to give the title compound (85 mg).

$^1$H-NMR (CDCl$_3$, 300 MHz) δ ppm: 0.86-1.40 (m, 6H), 1.46-2.00 (m, 7H), 2.10-4.05 (m, 12H), 2.95 (dd, J=14.1, 4.8 Hz, 1H), 4.10-4.55 (m, 3H).

IR (neat): 3368, 2927, 2853, 2237, 1695, 1574, 1450, 1418, 1384, 1347, 1279, 1258, 1157, 1082, 1008, 957, 893, 834, 756, 592 cm$^{-1}$.

INDUSTRIAL APPLICABILITY

The compounds of the present invention posses a sufficient sleep-inducing action; therefore, they are useful as a drug intended for sleep induction.

The invention claimed is:

1. A prostaglandin derivative represented by Formula (I):

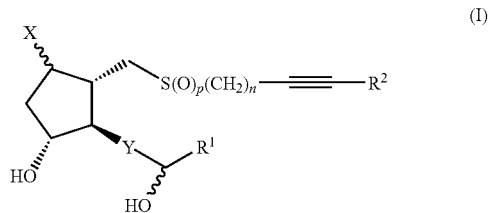

wherein X is a halogen atom in the β-substitution, Y is an ethynylene group, R$^1$ is a C$_{3-10}$ cycloalkyl group, R$^2$ is a CO$_2$R$^3$ group (R$^3$ is a hydrogen atom), n is an integer of 2 and p is 0,
a pharmaceutically acceptable salt thereof or a hydrate thereof.

2. The prostaglandin derivative represented by Formula (I) according to claim 1, wherein X is a chlorine atom in the β-substitution, Y is an ethynylene group, R$^1$ is cyclohexyl, R$^2$ is COOH, n is an integer of 2 and p is 0, a pharmaceutically acceptable salt thereof or a hydrate thereof.

3. A pharmaceutical composition comprising the prostaglandin derivative according to claim 1 or 2, a pharmaceutically acceptable salt thereof or a hydrate thereof.

\* \* \* \* \*